United States Patent
Kang et al.

(10) Patent No.: US 10,646,460 B2
(45) Date of Patent: *May 12, 2020

(54) PHARMACEUTICAL COMPOSITION FOR INHIBITING GROWTH OF CANCER STEM CELLS, CONTAINING ALDEHYDE INHIBITOR AND BIGUANIDE-BASED COMPOUND

(71) Applicant: NATIONAL CANCER CENTER, Gyeonggi-do (KR)

(72) Inventors: Seok Gu Kang, Gyeonggi-do (KR); Jong Hee Chang, Seoul (KR); Eui Hyun Kim, Seoul (KR); Ji Hyun Lee, Gyeonggi-do (KR); Yun Hee Jo, Seoul (KR); Junseong Park, Seoul (KR); Jin Kyoung Shim, Seoul (KR); Soo Youl Kim, Gyeonggi-do (KR)

(73) Assignee: National Cancer Center (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/400,514

(22) Filed: May 1, 2019

(65) Prior Publication Data
US 2019/0254995 A1    Aug. 22, 2019

Related U.S. Application Data

(63) Continuation of application No. 15/547,860, filed as application No. PCT/KR2016/001111 on Feb. 2, 2016, now abandoned.

(30) Foreign Application Priority Data

Feb. 2, 2015  (KR) ........................ 10-2015-0016295
Jan. 27, 2016  (KR) ........................ 10-2016-0010118

(51) Int. Cl.
A61K 31/155    (2006.01)
A61K 31/11    (2006.01)
(Continued)

(52) U.S. Cl.
CPC ............ *A61K 31/155* (2013.01); *A61K 31/11* (2013.01); *A61K 45/06* (2013.01); *A61P 35/00* (2018.01)

(58) Field of Classification Search
None
See application file for complete search history.

(56) References Cited

U.S. PATENT DOCUMENTS

2009/0010878 A1    1/2009  Holmlund et al.
2012/0114676 A1*   5/2012  Thompson ........... A61K 31/155
                                              424/184.1
(Continued)

FOREIGN PATENT DOCUMENTS

KR    10-2013-0015669    2/2013
KR    10-1242726         3/2013
KR    10-2015-0102152    9/2015

OTHER PUBLICATIONS

Appleyard, ML.V.C.L. et al., "Phenformin as Prophylaxis and Therapy in Breast Cancer Xenografts." British Journal of Cancer, 2012, vol. 106, No. 6, pp. 1117-1122.
(Continued)

Primary Examiner — Bong-Sook Baek
(74) Attorney, Agent, or Firm — Sheridan Ross P.C.

(57) ABSTRACT

The present invention relates to a pharmaceutical composition for inhibiting growth of cancer stem cells, containing an aldehyde inhibitor and a biguanide-based compound. The pharmaceutical composition according to the present invention contains a combination of an aldehyde inhibitor and a biguanide-based compound, which can effectively inhibit
(Continued)

the growth of cancer stem cells such as neurospheres and can also inhibit the proliferation, invasion and metastasis of cancer cells, thereby preventing and/or treating cancer such as brain cancer.

6 Claims, 8 Drawing Sheets

(51) Int. Cl.
*A61K 45/06* (2006.01)
*A61P 35/00* (2006.01)

(56) References Cited

U.S. PATENT DOCUMENTS

2012/0302629 A1* 11/2012 Wang .................. C12Q 1/6886
514/449
2018/0015056 A1 1/2018 Kang et al.

OTHER PUBLICATIONS

Dean et al. "Tumour Stem Cells and Drug Resistance," Nature Reviews Cancer, Apr. 2005, vol. 5, No. 4, pp. 275-284.
Jiang et al. "Instability of BCR-ABL Gene in Primary and Cultured Chronic Myeloid Leukemia Stem Cells," Journal of the National Cancer Institute, May 2007, vol. 99, No. 9, pp. 680-693.
Koppaka, V. et al., "Aldehyde Dehydrogenase Inhibitors: a Comprehensive Review of the Pharmacology, Mechanism of Action, Substrate Specificity, and Clinical Application." Pharmacological Reviews, 2012, vol. 64, No. 3, pp. 520-539.
Mego, M., "Telomerase Inhibitors in Anticancer Therapy Gossypol as a Potential Telomerase Inhibitor." Bratislayske Lekarske Listy, 2002, vol. 103, No. 10, pp. 378-381.
International Search Report prepared by the Korean Intellectual Property Office dated Jul. 29, 2016, for International Application No. PCT/KR2016/001111.
Official Action for U.S. Appl. No. 15/547,880, dated Oct. 9, 2018 14 pages.

* cited by examiner

PHARMACEUTICAL COMPOSITION FOR INHIBITING GROWTH OF CANCER STEM CELLS, CONTAINING ALDEHYDE INHIBITOR AND BIGUANIDE-BASED COMPOUND

CROSS REFERENCE TO RELATED APPLICATIONS

This application is continuation of U.S. patent application Ser. No. 15/547,860, filed, Aug. 1, 2017, which is a national stage application under 35 U.S.C. 371 and claims the benefit of PCT Application No. PCT/KR2016/001111 having an international filing date of Feb. 2, 2016, which designated the U.S., which PCT application claimed the benefit of Korean Patent Application No. KR 10-2015-0016295 filed Feb. 2, 2015, and Korean Patent Application No. KR 10-2016-0010118 filed Jan. 27, 2016, the disclosures of each of which are incorporated herein by reference.

TECHNICAL FIELD

The present invention relates to a pharmaceutical composition for inhibiting growth of cancer stem cells, containing an aldehyde inhibitor and a biguanide-based compound.

BACKGROUND ART

Cancer is one of the most common causes of death in the world. About 10 million new cancer cases occur each year, and cancer is responsible for about 12% of the total cause of death, making cancer the third leading cause of death.

Among various kinds of cancers, particularly brain cancer is characterized in that it occurs regardless of age and the frequency of occurrence thereof in infants is higher than that of other cancers. Brain cancer collectively refers to primary brain cancer, which occurs in brain tissue and meninges surrounding the brain, and secondary brain cancer metastasized from cancer that occurred in the cranium or other areas of the body. This brain cancer differs in many respects from cancers that occur in other organs. Specifically, cancers that occur in the stomach, lung, breast and the like are limited to one or two kinds in each organ and generally have identical or similar characteristics. However, in the brain, very various kinds of cancers occur, including, for example, glioblastoma multiforme, malignant glioma, lymphoma, germinoma, metastatic tumors, and the like.

Among these brain cancers, glioma, particularly glioblastoma multiforme (GBM), is the most malignant and aggressive form of brain cancer, and thus is a very fetal disease that has a very poor prognosis and shows an average survival period of about 1 year or less after diagnosis. Since the boundary between brain cells and tumor cells is indistinct, it is almost impossible to completely remove GBM by surgery.

Despite an advance in the field of cancer treatment, current leading therapies include surgery, radiation and chemotherapy. Chemotherapeutic approaches are mainly used for treatment of, metastatic or particularly, aggressive cancer. Most of the cancer therapeutic agents that are currently used in clinical practice are cytotoxins. Cytotoxic agents work by damaging or killing cells that exhibit rapid growth.

Ideal cytotoxic agents would have specificity for cancer and tumor cells, while not affecting normal cells. Unfortunately, such ideal cytotoxic agents have not been found, and instead agents that target especially rapidly dividing cells (both tumor and normal) have been used. Accordingly, materials that are cytotoxic to cancer cells while exerting only mild effects on normal cells are highly desirable. In fact, recent many studies have been focused on the development of alternative anticancer agents that can particularly inhibit the growth of tumor cells.

Accordingly, the development of chemotherapeutic agents other than surgical therapy is urgently required, but effective therapeutic methods have not yet been developed, and thus the research and development thereof is required.

DISCLOSURE

Technical Problem

An object of the present invention is to provide a pharmaceutical composition that can effectively inhibit the growth of cancer stem cells to inhibit the proliferation, invasion and metastasis of cancer cells, thereby preventing and/or treating cancer.

Technical Solution

The present inventors have conducted extensive studies, and as a result, have found that co-administration of an aldehyde inhibitor and a biguanide-based compound can inhibit the growth of cancer stem cells to inhibit the proliferation, invasion and metastasis of cancer cells to thereby prevent and/or treat cancer. Based on this finding, the present invention has been accomplished.

As used herein, the term "cancer stem cells" generally refers to cancer cells having self-renewal or differentiation potential which is the characteristic potential that is characteristic of stem cells. For example, cancer stem cells may include neurospheres that are stem cell in the brain's central nervous system. In the normal tumor growth conditions of cancer stem cells (the "normal tumor growth conditions" refers to a state in which a nutrient (glucose) required for cell growth is sufficient and conditions for tumor microenvironment growth are abundant, and thus there is no cell stress), the cancer stem cells may proliferate at a slow rate, unlike general cancer cells, or may be maintained in a dormant state, and thus may have resistance to anticancer agents. For example, expression of transcription regulators such as PGC-1a may be controlled, unlike that in normal tumor cells, and thus the function of major metabolism regulatory substances therein may differ from that in general cancer cells. Thus, the term "cancer stem cells" generally refers to cells that acquire resistance to apoptosis in a nutrient-deficient state through this different metabolism regulatory ability and the regulation of cell signaling systems mechanistically linked thereto, and have invasive and/or metastatic potential. However, the cancer stem cells are not limited thereto and may include any cells that may differentiate into general cancer cells.

As used herein, the expression "inhibiting the growth of cancer stem cells" is meant to include inhibition of cancer stem cell maintenance, inhibition of cancer stem cell malignancy, and inhibition of cancer stem cell invasion.

Specifically, the present invention is directed to a pharmaceutical composition for inhibiting growth of cancer stem cells, containing an aldehyde inhibitor and a biguanide-based compound. Preferably, the aldehyde inhibitor may be gossypol, and the biguanide-based compound may be phenformin.

Herein, "the gossypol" is a phenol derivative that is contained in large amounts in cotton plants. In China, it was found that this gossypol inhibits male sperm function. Thus, the gossypol has been studied for use as male oral contraceptives. Furthermore, "the phenformin" is generally known as a diabetes therapeutic agent that physiologically regulates carbohydrate metabolism and lipid metabolism.

In the present invention, a combination of the gossypol and the phenformin preferably exhibits a very high synergistic effect on the inhibition of growth of cancer stem cells. Herein, the gossypol is preferably a compound represented by the following formula 1 or its derivative, but is not limited thereto, and the phenformin is preferably a compound represented by the following formula 2 or its derivative, but is not limited thereto:

Formula 1

Formula 2

In the pharmaceutical composition of the present invention, the aldehyde inhibitor and the biguanide-based compound may be contained at a weight ratio of 1:1 to 100, preferably 1:2 to 20.

Furthermore, in the pharmaceutical composition of the present invention, the aldehyde inhibitor may be contained in an amount of 0.5 to 50 μM.

Moreover, in the pharmaceutical composition of the present invention, the biguanide-based compound may be contained in an amount of 10 to 1000 μM.

As described above, the composition of the present invention may inhibit the growth of cancer stem cells to thereby prevent and/or treat a cancer selected from the group consisting of uterine cancer, breast cancer, gastric cancer, brain cancer, rectal cancer, colorectal cancer, skin cancer, blood cancer and liver cancer. Preferably, the composition of the present invention may inhibit the proliferation, maintenance, malignancy and invasion abilities of neurospheres to thereby effectively prevent and/or treat, brain cancer, particularly, glioblastoma.

However, the pharmaceutical composition of the present invention may be co-administered with other additional anticancer agents in order to effectively treat not only cancer stem cells, but also general cancer cells.

The anticancer that may be used in the present invention may be one or more selected from the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, viscum album, asparaginase, tretinoin, hydroxycarbamide, dasatinib, estramustine, gemtuxumab ozogamicin, ibritumomab tiuxetan, heptaplatin, methylaminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastin, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine and carmustine, but is not limited thereto.

In the present invention, the pharmaceutical composition may be in the form of capsules, tablets, granules, injectable solutions, ointments, powders or beverages. The pharmaceutical composition may be for administration to humans.

For use, the pharmaceutical composition of the present invention may be formulated as oral preparations, including powders, granules, capsules, tablets, aqueous suspensions and the like, skin external preparations, suppositories, and sterile injectable solutions, according to conventional methods, but is not limited thereto. The pharmaceutical composition of the present invention may contain a pharmaceutically acceptable carrier. Pharmaceutically acceptable carriers that may be used in the present invention include binders, lubricants, disintegrants, excipients, solubilizers, dispersing agents, stabilizers, suspending agents, pigments, fragrances and the like, which may be used for oral administration; buffers, preservatives, pain-relieving agents, solubilizers, isotonic agents, stabilizers and the like, which may be used for injection; and bases, excipients, lubricants, preservatives and the like, which may be used for local administration. The pharmaceutical composition of the present invention may be formulated in various ways by mixing it with the pharmaceutically acceptable carrier as described above. For example, for oral administration, the pharmaceutical composition of the present invention may be formulated as tablets, troches, capsules, elixirs, suspensions, syrups, wafers or the like, and for injection, may be formulated as unit dose ampoules or multi-dose vials. In addition, the pharmaceutical composition of the present invention may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition of the present invention may further contain a filler, an anticoagulant, a lubricant, a wetting agent, a fragrance, an emulsifier, a preservative or the like.

The routes of administration of the pharmaceutical composition according to the present invention include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred. As used herein, the term "parenteral" is meant to include subcutaneous, transdermal, intravenous, intramuscular, intra-articular, intra-synovial, intrasternal, intradural, intra-lesional and intra-cranial injection or infusion techniques. The pharmaceutical composition of the present invention may also be formulated as suppositories for intrarectal administration.

The pharmaceutical composition of the present invention may vary depending on various factors, including the activity of specific compounds used, the patient's age, body weight, general health, sex, diet, the period of administration, the route of administration, excretion rate, the drug content, and the severity of a specific disease to be prevented or treated. The dose of the pharmaceutical composition may be suitably selected by a person skilled in the art depending on the patient's condition, body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present invention in any way. The pharmaceutical composition according to the present invention may be formulated as pills, sugar-coated tablets, capsules, liquids, gels, syrups, slurries, or suspensions.

Advantageous Effects

The pharmaceutical composition according to the present invention contains a combination of an aldehyde inhibitor and a biguanide-based compound, which may effectively inhibit the growth of cancer stem cells such as neurospheres and may also inhibit the proliferation, invasion and metastasis of cancer cells, thereby preventing and/or treating cancer such as brain cancer.

BEST MODE

The present invention provides a pharmaceutical composition containing a combination of an aldehyde inhibitor and a biguanide-based compound, which may effectively the growth of cancer stem cells such as neurospheres to inhibit the proliferation, invasion and metastasis of cancer cells, thereby preventing and/or treating cancer such as brain cancer.

MODE FOR INVENTION

Hereinafter, the present invention will be described in further detail with reference to examples. It will be obvious to those skilled in the art that these examples are for illustrative purposes and are not intended to limit the scope of the present invention.

EXAMPLES

Reference Example 1: Analysis of Cell Viability Following Treatment with Gossypol U87 cells (GBM cells) were treated with 0.5, 1, 5, 10 and 50 µM of gossypol for 72 hours (FIG. 1).

Figure 1:
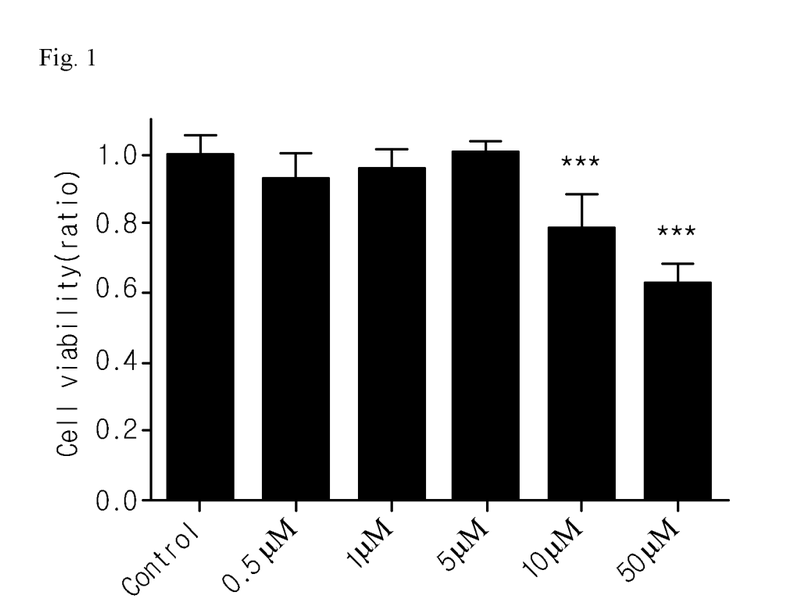
FIG. 1 graphically shows the results of MTT assay performed at varying concentrations of gossypol in Reference Example 1.

As can be seen in FIG. 1, when the cells were treated with each concentration of gossypol for 72 hours, growth of the cells was inhibited.

Experimental Example 1: Analysis of Cell Viability Following Treatment with a Combination of Gossypol and Phenformin U87 cells were seeded onto a 96-well plate and cultured at 37° C. for 24 hours. Then, the cells were treated with each of pharmaceutical compositions of Examples and Comparative Examples as shown in Table 1 below, after which the cells were treated with MTS reagent at a concentration of 20 µL/well and incubated at 37° C. for 4 hours. Next, the absorbance at 490 nm was measured, and then the change in absorbance relative to an untreated control group was calculated to determine cell viability. The results are graphically shown in FIG. 2.

TABLE 1

| | Composition |
|---|---|
| Comparative Example 1 | — |
| Comparative Example 2 | 0.5 µM gossypol |
| Comparative Example 3 | 1 µM gossypol |
| Comparative Example 4 | 10 µM phenformin |
| Example 1 | 10 µM phenformin + 0.5 µM gossypol |
| Example 2 | 10 µM phenformin + 1 µM gossypol |

Figure 2:
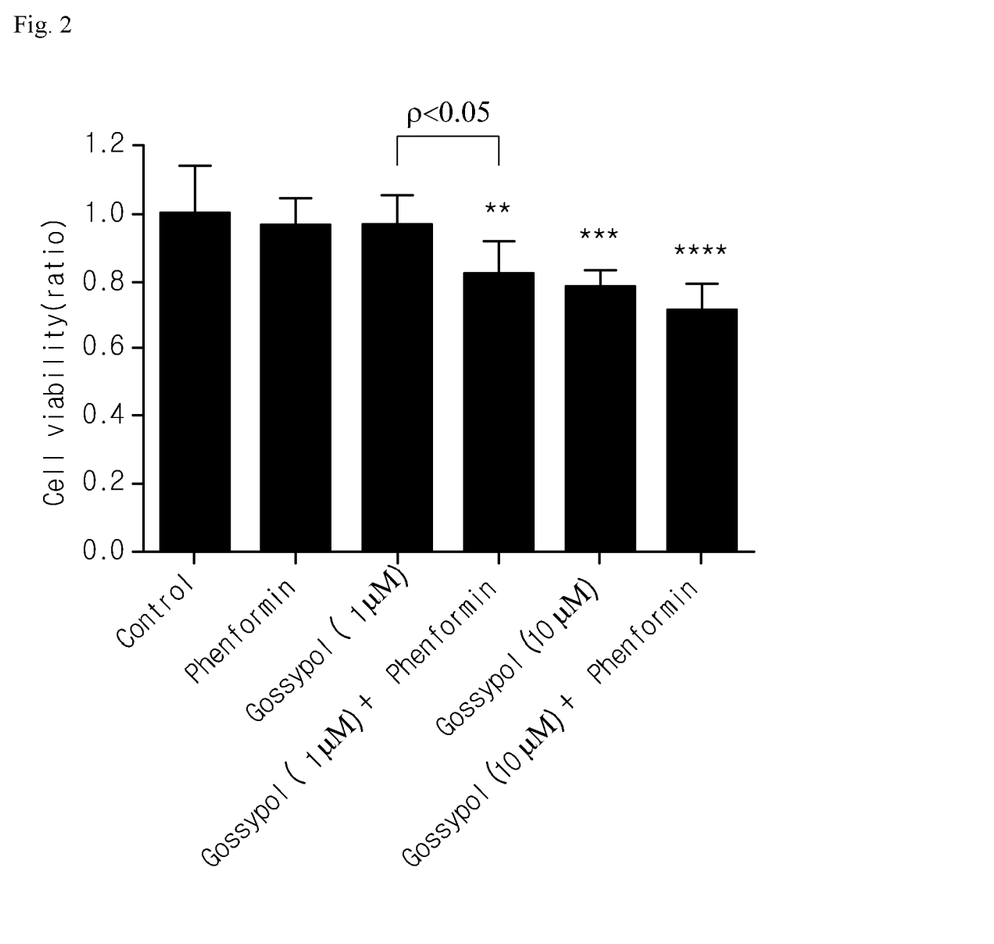
FIG. 2 graphically shows the change in viability of U87 cells by treatment with each of compositions of Examples and Comparative Examples in Experimental Example 1.

As can be seen in FIG. 2, the viability of the cells significantly decreased when the cells were treated with a combination of gossypol and phenformin compared to when the cells were treated with gossypol or phenformin alone.

Experimental Example 2: Analysis of Formation of Neurospheres

U87 cells were cultured in DMEM/F-12 medium containing 2 wt % 1×B27, 0.02 wt % bFGF (20 ng/ml), 0.02 wt % EGF (20 ng/ml) and 50 U/ml penicillin-50 mg/ml streptomycin (100×, Gibco, Invitrogen Korea, Seoul, South Korea) to form tumor spheres. Next, the cells were seeded onto a 96-well plate at a density of 10 cells/well and treated with each of 1 µM gossypol, 10 µM phenformin and a mixture of 1 µM gossypol and 10 µM phenformin. Then, the cells were cultured at 37° C. for 3 weeks. To observe the morphology and size of the U87 cells, the obtained cell cultures were observed with an inverted phase-contrast microscope) (1×71

Figure 3:
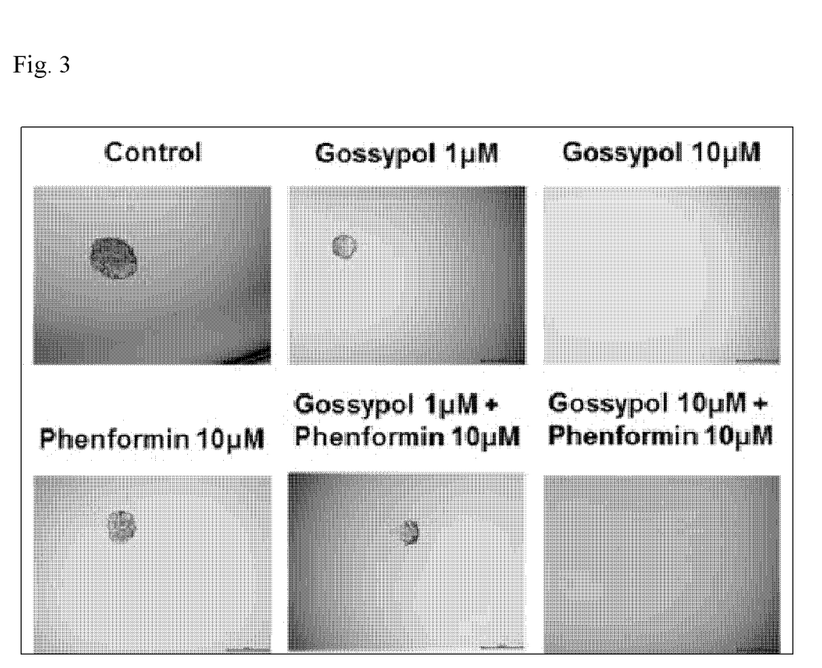
FIG. 3 shows photographs of U87 neurosphere cells following each treatment in Experimental Example 2.

Inverted Microscope; Olympus, Tokyo, Japan) and photographed with a digital camera (DP70 Digital Microscope Camera; Olympus). The photographs are shown in FIG. 3. In addition, the change in radius of neurospheres by each treatment is graphically shown in FIG. 4, and the degree of formation of neurospheres is graphically shown in FIG. 5.

Figure 4:
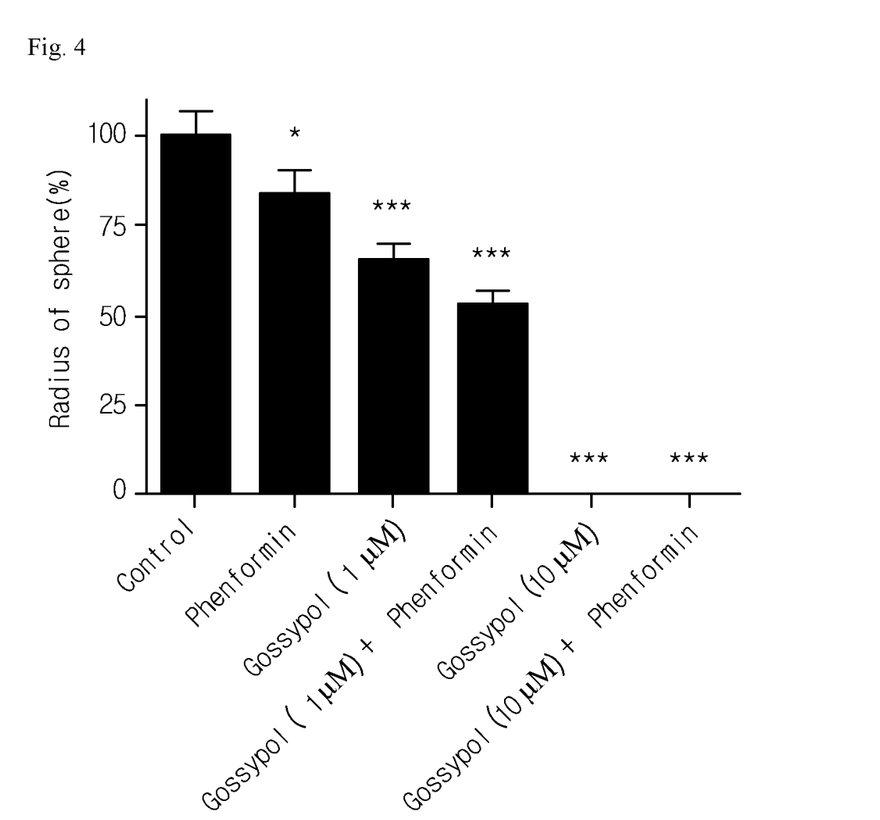
FIG. 4 graphically shows the change in radius of U87 neurosphere cells following each treatment in Experimental Example 2.
Figure 5:
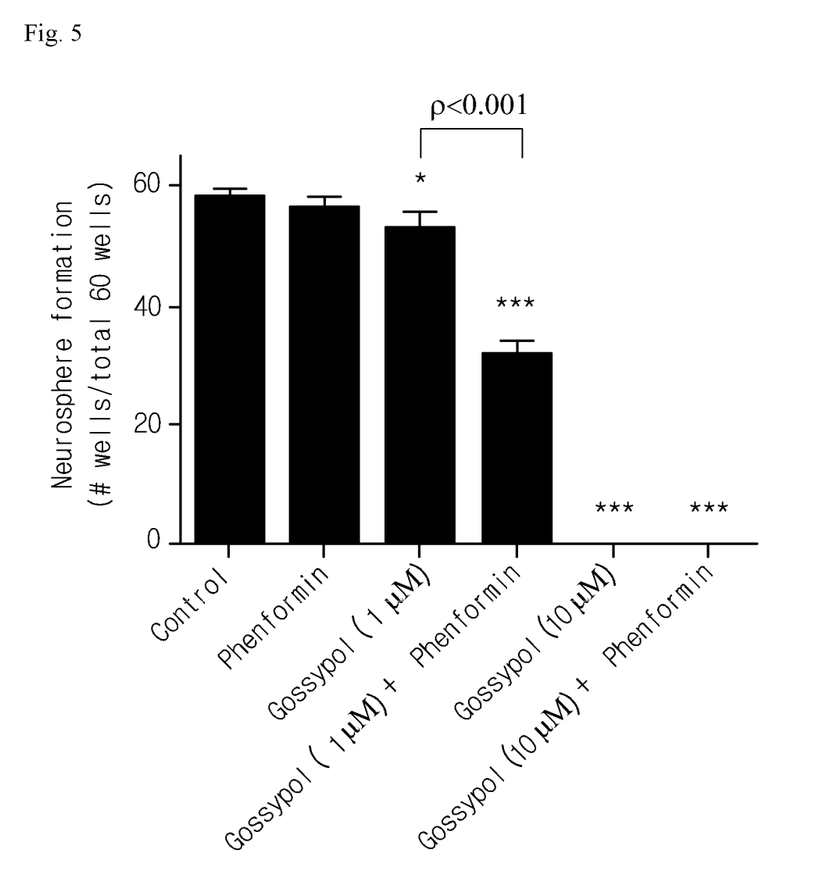
FIG. 5 graphically shows the degree of formation of U87 neurosphere cells following each treatment in Experimental Example 2.

In FIG. 4, the percent change in the radius of the neurospheres is expressed as the percentage of the average radius of the neurospheres after each treatment relative to the average radius of the neurospheres seeded onto the 96-well plate, and in FIG. 5, the degree of neurosphere formation is expressed as the percentage of the number of the neurosphere cells after each treatment relative to the number of the neurosphere cells seeded onto the 96-well plate.

As can be seen in the cell photographs of FIG. 3, even when the neurosphere cells were treated with gossypol or phenformin alone, the size of the neurosphere cells decreased, but when the neurosphere cells were treated with a combination of gossypol and phenformin, no neurosphere cells were observed.

Furthermore, as can be seen in FIGS. 4 and 5, the radius of the neurosphere cells significantly decreased when the cells were treated with a combination of gossypol and phenformin compared to when the cells were treated with gossypol or phenformin alone, and the number of the neurosphere cells also significantly decreased when treated with a combination of gossypol and phenformin.

Experimental Example 3: Transwell Invasion Assay

Figure 6:
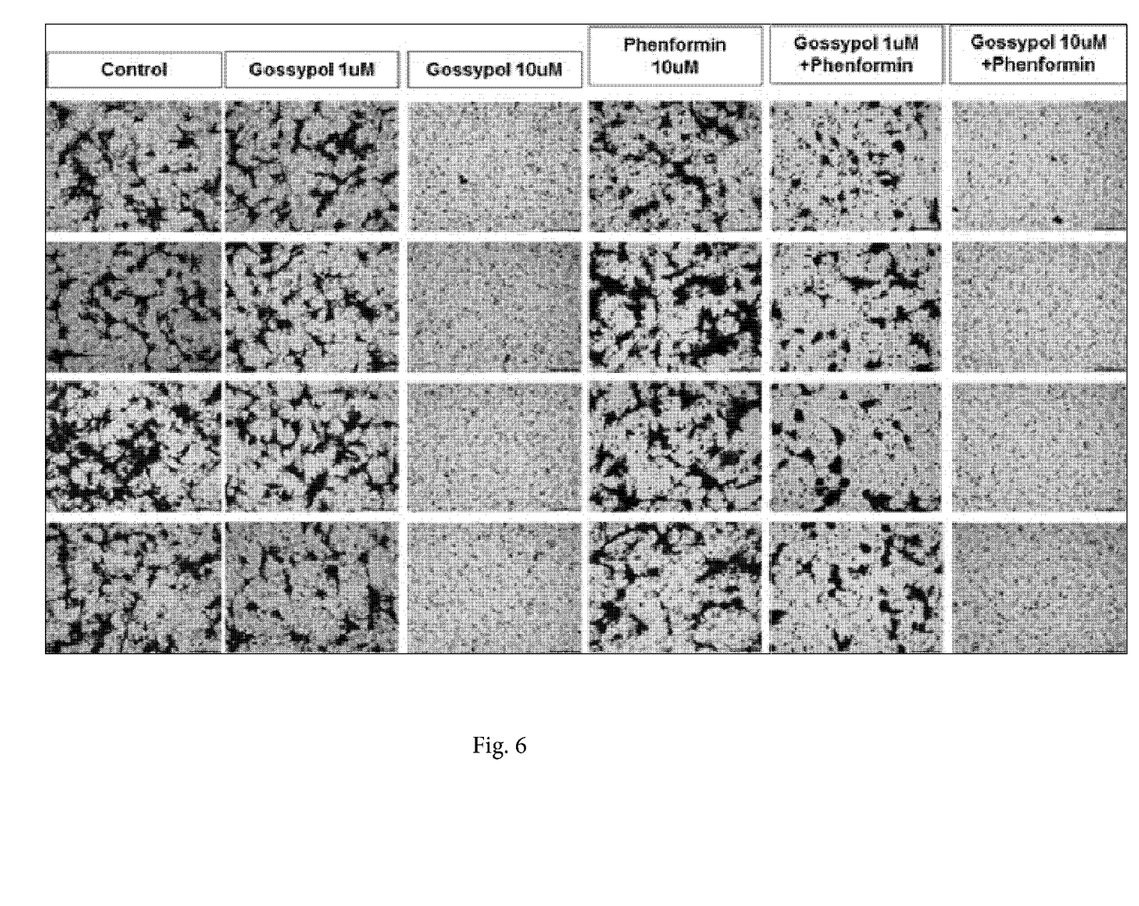
FIG. 6 shows photographs of U87 neurosphere cells following each treatment in Experimental Example 3.

U87 cells ($2\times10^5$ cells/well) were suspended in 0.1 ml of growth medium, and then treated with 1 µM gossypol, 10 µM phenformin or a mixture of 1 µM gossypol and 10 µM phenformin and loaded into the upper wells of a transwell chamber (8 mm pore size; Corning Glass). Herein, the upper portion of the transwell chamber was filled with 0.5 ml of growth medium, and the upper portion was pre-coated with 8.4 mg/ml of Matrigel (Corning Matrigel Matrix) with reduced growth factors. The cells were cultured in the chamber at 37° C. for 48 hours, and then the non-invaded cells on the upper surface of the filter were removed with cotton swabs. The cells that migrated to the lower surface of the filter were fixed and stained with a Diff-Quick kit (Fisher), and then the obtained cell cultures were observed with a phase-contrast microscope (Olympus). Photographs of the cell cultures are shown in FIG. 6. For measurement of cell invasion, the number of cells in 10 microscopic fields per well was counted.

As can be seen in FIG. 6, the radius of the neurosphere cells significantly decreased when the cells were treated with a combination of gossypol and phenformin compared to when the cells were treated with gossypol or phenformin alone, and the number of the neurosphere cells also significantly decreased when treated with a combination of gossypol and phenformin.

This suggests that treatment with a combination of gossypol and phenformin according to the present invention may effectively inhibit the proliferation and metastasis of brain cancer stem cells, compared to treatment with gossypol or phenformin alone, thereby significantly increasing the effect of treating brain cancer.

Experimental Example 4: Evaluation of Gossypol Effect in Orthotopic Xenograft Models Gossypol and phenformin to be used in an animal study were dissolved in DMSO and PBS, respectively. A composition for co-administration of gossypol and phenformin was dissolved in PBS containing 10 wt % DMSO and 10 wt % cremophor.

For preparation of orthotopic xenograft models, 4-8-week-old male athymic nude mice (Central Lab., Korea) were used. For stabilization, the mice were maintained in a sterilized environment for at least one week before use in the experiment while they were fed with a sufficient diet. All protocols in the animal study were approved by the Institutional Animal Care and Use Committee of Yonsei University. First, the mice were anesthetized by intraperitoneal injection of 30 mg/kg of Zoletil and 10 mg/kg of Xylazine, and $2\times10^5$ U87-luc cells were transplanted into the right frontal lobe of the cerebrum to a depth of 4.5 mm by use of a Hamilton syringe. The U87-luci cells were injected into five mice of the same group at the same time at a rate of 0.5 l/minute by use of a micro-infusion syringe pump. Thereafter, the mice were administered orally with gossypol (40 mg/kg) and/or phenformin (100 mg/kg) each day. Mouse groups according to the kind of drug administered are shown in Table 2 below.

TABLE 2

| | Kind of drug administered |
|---|---|
| Comparative Example 6 | Administration of distilled water after transplantation of U87-leu cells |
| Example 4 | Administration of gossypol alone after transplantation of U87-leu cells |
| Example 5 | Administration of phenformin alone after transplantation of U87-leu cells |
| Example 6 | Co-administration of gossypol and phenformin after transplantation of U87-leu cells |

An increase or decrease in the body weight was checked each day, and when a mouse whose body weight decreased by 15 wt % compared to the body weight before the start of the experiment, the mouse was euthanized according to the approved protocol.

Collection and analysis of bioluminescence were performed using an IVIS Imaging System and an image analysis program (Living Image V4.2 software). For this, at 15 minutes before signal measurement, 100 µl of d-luciferin (30 mg/mL PBS) was intraperitoneally injected into each mouse under anesthesia with 2.5% isoflurane. Signal measurement was performed for 5 seconds at 1, 3 and 5 weeks after transplantation of the U87-luc cells. The results are shown in FIG. 7.

Figure 7:
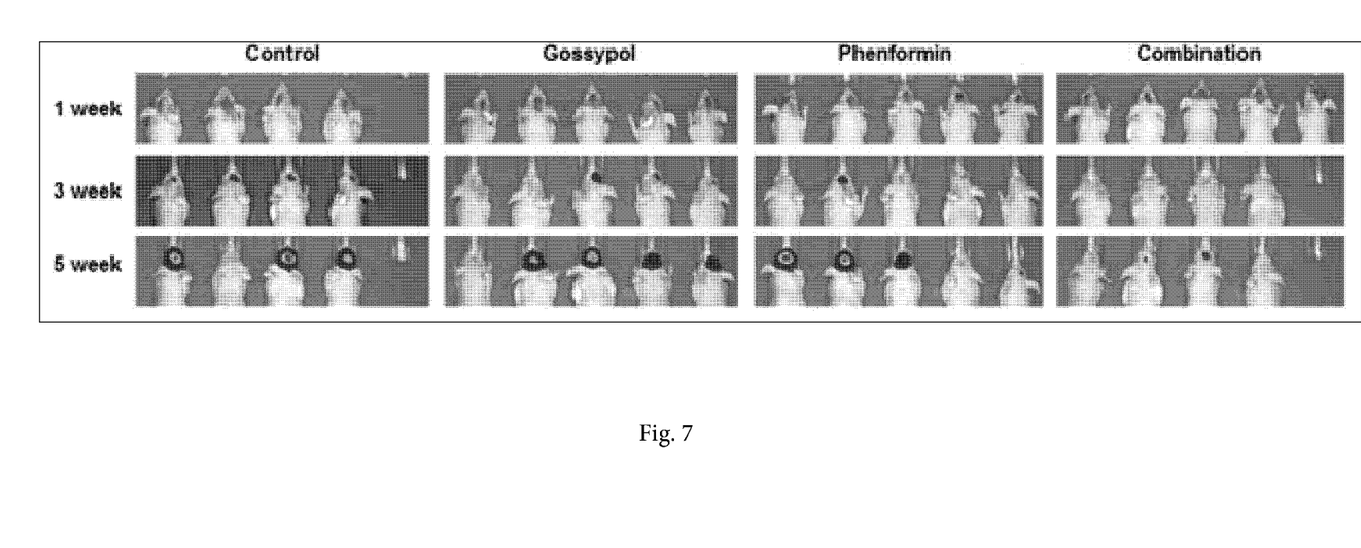
FIG. 7 shows the degree of occurrence of brain cancer in orthotopic xenograft model mice following each treatment in Experimental Example 4.
Figure 8:
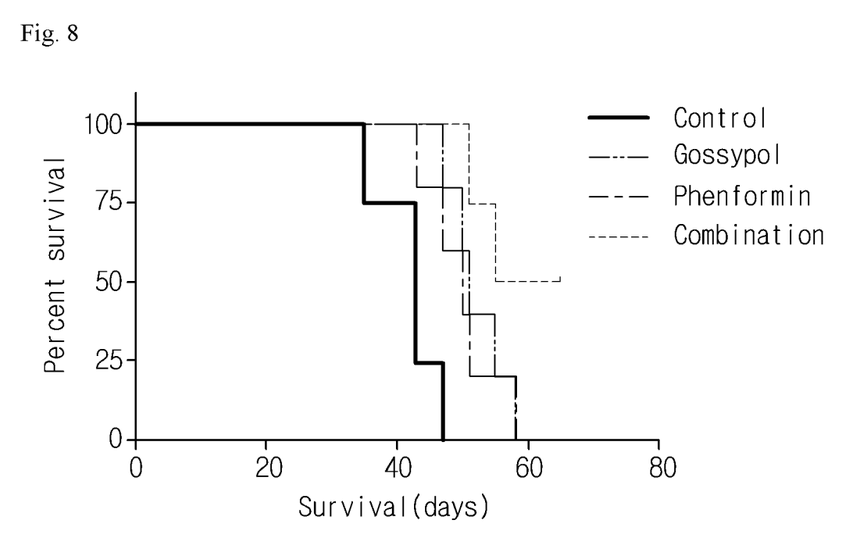
FIG. 8 shows the survival rate of orthotopic xenograft model mice following each treatment in Experimental Example 4.

The experimental results obtained using the orthotopic xenograft models are shown in FIG. 7. As can be seen therein, at 5 weeks after transplantation of the cells, fluorescence was observed in Comparative Example 6, Example 4 (administration of gossypol alone) and Example 5 (administration of phenformin alone), indicating that brain cancer was caused by the U87-luc cells, but Example 6 (co-administration of gossypol and phenformin) showed a very low level of brain cancer compared to Comparative Example 6, Examples 4 and 5. In addition, the results of measuring the survival rate of the mice (FIG. 8) indicated that the survival rate of the mouse group of Example 6 was higher than those of the mouse groups of Comparative Example 6 and Examples 4 and 5.

Although the embodiments of the present invention have been described in detail, it will be obvious to those skilled in the art that the scope of the present invention is not limited to these embodiments and that various changes and modifications are possible without departing from the technical spirit of the present invention as defined in the appended claims.

INDUSTRIAL APPLICABILITY

As described above, the pharmaceutical composition according to the present invention contains a combination of an aldehyde inhibitor and a biguanide-based compound, which can effectively inhibit the growth of cancer stem cells such as neurospheres and can also inhibit the proliferation, invasion and metastasis of cancer cells, thereby preventing and/or treating cancer such as brain cancer.

The invention claimed is:

1. A method for inhibiting growth of brain cancer stem cells in a subject suffering from brain cancer, comprising administering gossypol and phenformin to the subject, wherein the administration of gossypol and phenformin has a synergistic anti-cancer effect.

2. The method of claim 1, wherein the gossypol and phenformin are administered at a weight ratio of 1:1 to 100.

3. The method of claim 1, wherein the gossypol and phenformin are administered at a weight ratio of 1:2 to 20.

4. The method of claim 1, wherein the gossypol is administered in an amount of 0.5 to 50 μM.

5. The method of claim 1, wherein the phenformin is administered in an amount of 10 to 1000 μM.

6. The method of claim 1, wherein the inhibiting of the growth of the brain cancer stem cells is inhibition of brain cancer stem cell maintenance, inhibition of brain cancer stem cell malignancy, or inhibition of brain cancer stem cell invasion.

* * * * *